United States Patent [19]

Pianetti

[11] Patent Number: 5,433,217
[45] Date of Patent: Jul. 18, 1995

[54] BIMETALLIC SPIRAL INTRAUTERINE DEVICE

[76] Inventor: Francesco Pianetti, Via Turati, 22-20013 Magenta (Prov. of Milan), Italy

[21] Appl. No.: 158,494

[22] Filed: Nov. 29, 1993

Related U.S. Application Data

[63] Continuation of Ser. No. 466,334, filed as PCT/EP89/01060, Sep. 12, 1989, published as WO90/02478, Mar. 22, 1990, abandoned.

[30] Foreign Application Priority Data

Sep. 14, 1988 [IT] Italy .......................... 21923 A/88

[51] Int. Cl.⁶ .................................................. A61F 6/06
[52] U.S. Cl. ...................................... 128/830; 128/833
[58] Field of Search .................................. 128/830–841

[56] References Cited

U.S. PATENT DOCUMENTS

| | | | |
|---|---|---|---|
| 3,563,235 | 2/1971 | Zipper | 128/833 |
| 3,937,217 | 2/1976 | Kosonen | 128/839 |
| 3,973,560 | 8/1976 | Emmett | 128/833 |
| 4,040,417 | 8/1977 | Zipper | 128/833 |
| 4,198,966 | 4/1980 | Kaivola | 128/839 |
| 4,326,511 | 4/1982 | Zimerman | 128/833 |
| 4,351,326 | 9/1982 | Kosonen | 128/833 |
| 4,353,363 | 10/1982 | Sopena Quesada | 128/833 |
| 4,562,835 | 1/1986 | Anderson | 128/839 |
| 4,655,204 | 4/1987 | Basuyaux | 128/839 |
| 4,932,421 | 6/1990 | Kaali | 128/831 |

FOREIGN PATENT DOCUMENTS 0191957 12/1985 European Pat. Off. .
2207939 2/1972 Germany .

OTHER PUBLICATIONS

Inhibition of Sperm Motility In Vitro by Copper Wire, By Ullmann et al. Contraception, vol. 6, No. 1 Jul. 1972 pp. 71–76.
Copper IUD: Enhancement of its Efficacy by the Addition of Silver and Nickel By Kressero et al., Contraception, vol. 9, No. 2—Feb. 1974 pp. 141–151.

*Primary Examiner*—Michael A. Brown

[57] ABSTRACT

Intrauterine device having a spiral (1,2) wound on a plastic material support (3). The spiral comprises a pair of different metals welded together or being in close reciprocal contact. The spiral is in contact with the uterine environment.

9 Claims, 2 Drawing Sheets

5,433,217

BIMETALLIC SPIRAL INTRAUTERINE DEVICE

This application is a continuation of application Ser. No. 07/466,334, filed as PCT/EP89/01060, Sep. 12, 1989, published as WO90/02478, Mar. 22, 1990, now abandoned.

FIELD OF THE INVENTION

The present invention refers to an intrauterine device consisting of a metallic spiral.

PRIOR ART

Metallic spiral intrauterine devices wound on a plastic material support are known.

Furthermore, studies were published on the contraceptive effect of metals, for istance:

Ullmann G., Hammerstein J.: Inhibition of sperm, mobility in vitro by copper wire; Contraception 6:71, 1972.

Furthermore, devices are also known consisting of rings separatly mounted on plastic material supports, said rings consisting of two different metals. (E. Kesserü, Hurtado, B. Muhe: Copper IUD, Enhancement of its efficacy by addition of silver and nickel; Contraception, February 1974, vol. 9, n. 2). Said devices have been in use for a long time; however, the need was felt for more efficient devices.

SUMMARY

We have now surprisingly found an intrauterine device having a decidedly higher efficency than the ones previously known.

Said device comprises a spiral wound on a plastic material support, and is characterised in that said spiral consists of a pair of different metals in close contact with each other and both in contact with the uterine environment.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The characteristics and advantages of tile device according to the present invention will now be described in detail with reference to preferred embodiments of the invention, which are reported only to illustrate the invention without limiting it.

In FIGS. 1 to 4, a first embodiment of the device according to the invention is illustrated, while FIGS. 5 to 7 and 8 to 12 illustrate, respectively, a second and a third embodiment.

Figure 1:
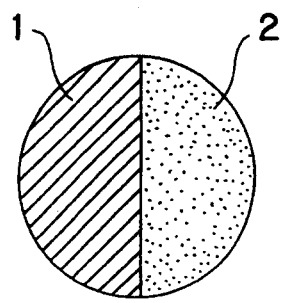
FIGS. 1 and 2 are cross-sectional views of two metal wires used in a first embodiment of the present invention.
Figure 2:
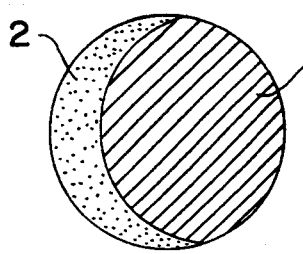

Referring to the different figures and to time reference numerals in them, FIGS. 1 and 2 represent cross sections of two metal wires, each consisting of two different metals, respectively 1 and 2, welded together along their length.

As can be seen comparing the two Figures, elements 1 and 2, welded together to form tile wires, may be prepared in different shapes, according to the desired contact extent.

Figure 3:
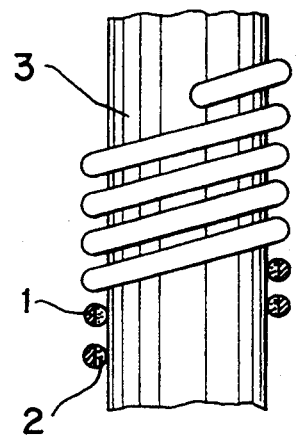
FIG. 3 is a partial side view of the first embodiment of the present invention.
Figure 4:
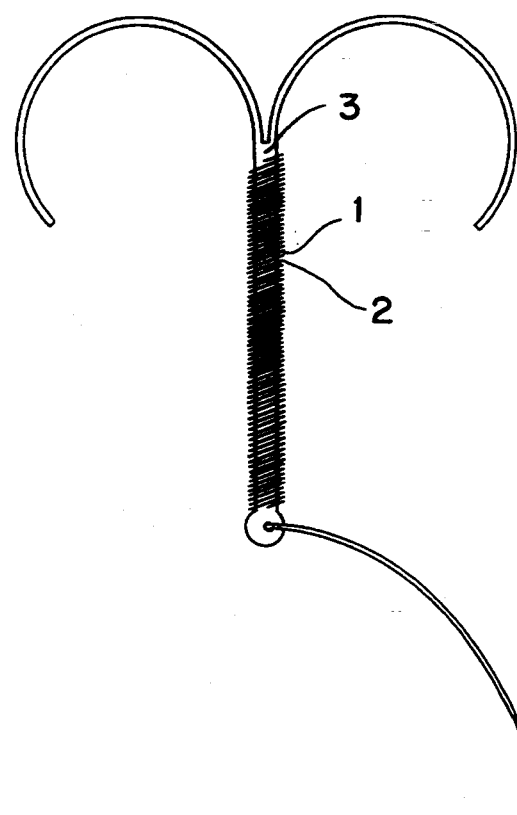
FIG. 4 is a complete side view of the first embodiment of the present invention.
Figure 5:
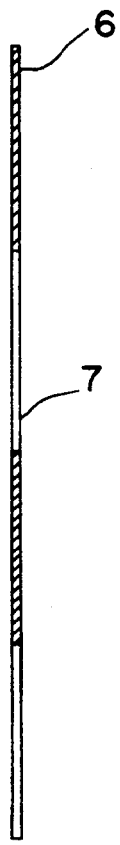
FIG. 5 is a sectional view of two metal wires used in a second embodiment of the present invention.
Figure 6:
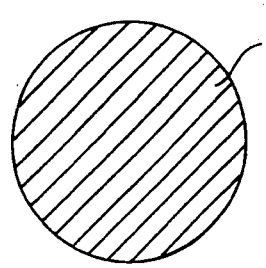
FIGS. 6 is a cross-sectional view of a first wire of the second embodiment of the present invention.
Figure 7:
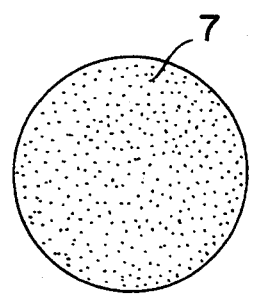
FIG. 7 is a cross-sectional view of a second wire of the second emobidment of the present invention.
Figure 8:
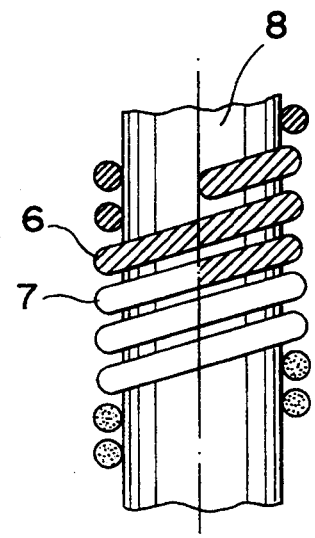
FIG. 8 is a partial side view of the second embodiment of the present invention.
Figure 9:
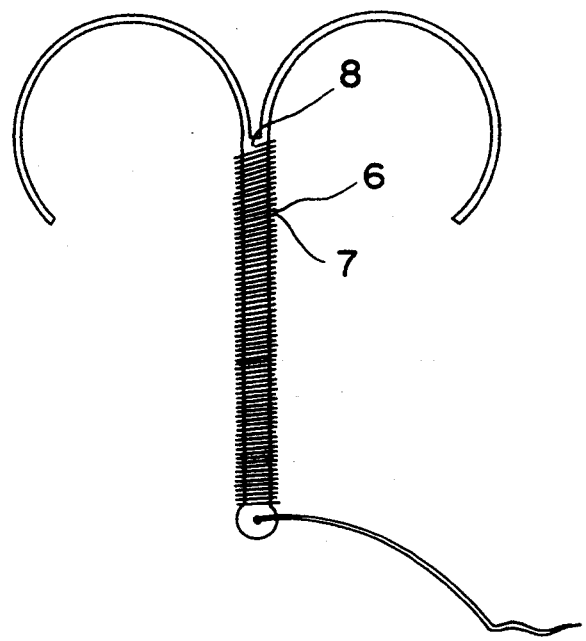
FIG. 9 is a complete side view of the second embodiment of the present invention.

With one of the wires described, a spiral is wound around the plastic material support 3 as represented in the details of FIG. 3, and in the complete device represented in FIG. 4. FIGS. 5, 6 and 7 represent, respectively, in longitudinal and traverse sections, a metal wire consisting of alternating segments 6 and 7 of two different metals welded together. The wire is applied as a spiral on a plastic material support 3 as indicated in the detail illustrated in FIG. 8 and in the complete device shown in FIG. 9.

The spiral wound wire has in all cases a length of 20-21 cm, while its diameter is of 0.15-0.30 min.

Different pairs of metals can be employed according to the present invention, provided that they do not exert a damaging action on the uterine structures.

Preferred pairs of metals are:

1—copper-silver
2—copper-iron
3—copper-nickel
4—iron-silver
5—iron-nickel
6—silver-nickel Particularly preferred is the copper-silver pair.

The device according to the invention exerts a decidedly higher contraceptive action with respect to known devices.

Said higher activity may be hypothetically referred to as a galvanic effect of the two metals being in strict contact in the uterine environment.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. An intrauterine device comprising a spiral and a plastic material support having a uniform diameter, the spiral being wound on the plastic material support and extending between both ends of the plastic material support, the spiral and plastic material support being placed in a uterine environment, the spiral consisting of a wire of two different metals welded together in alternating segments and both metals being in contact with the uterine environment.

2. The intrauterine device according to claim 1, wherein the two different metals are one of the pairs of copper-silver, copper-iron, copper-nickel, iron-silver, iron-nickel and silver-nickel.

3. The intrauterine device according to claim 1, wherein said wire forming the spiral has a length of 20 to 21 cm and a diameter of 0.15 to 0.30 mm.

4. The intrauterine device according to claim 1, wherein the spiral is uniformly wound around the plastic material support with a generally constant pitch to thereby encircle a portion of the plastic material support, the plastic material support is generally smooth and without interruptions at the portion thereof encircled by the spiral and all of the plastic material support between ends of the spiral being encircled by the spiral.

5. The intrauterine device according to claim 4, wherein the two metal forming the spiral are welded together so that the spiral has a generally uniform circular cross-section.

6. The intrauterine device according to claim 1, wherein the spiral is uniformly wound around the plastic material support with a constant pitch.

7. The intrauterine device according to claim 1, wherein the spiral has two ends and the spiral encircles a portion of the plastic material support and wherein the plastic material support only extends outwardly from the spiral at the two ends of the spiral.

8. The intrauterine device according to claim 1, wherein the plastic material support is generally smooth and without interruptions in an area encircled by the spiral.

9. An intrauterine device comprising a spiral and a plastic material support having a uniform diameter, the spiral being would on the plastic material support and extending between both ends of the plastic material support, the spiral and plastic material support being placed in a uterine environment, the spiral comprising two different metals welded together in alternating segments and having a generally uniform circular cross-section, both metals being in direct contact with the uterine environment, the spiral being uniformly wound around the plastic material support with a constant pitch to thereby encircle a portion of the plastic material support, the plastic material support being smooth and without interruptions at the portion thereof encircled by the spiral and all of the plastic material support between ends of the spiral being encircled by the spiral such that the plastic material support only extends outwardly from the spiral at the ends of the spiral.

* * * * *